United States Patent
Brown et al.

(10) Patent No.: US 8,043,366 B2
(45) Date of Patent: Oct. 25, 2011

(54) OVERLAPPING STENT

(75) Inventors: Brian J. Brown, Hanover, MN (US); Andrzej Malewicz, Minneapolis, MN (US); Daniel Gregorich, St. Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 411 days.

(21) Appl. No.: 11/221,618

(22) Filed: Sep. 8, 2005

(65) Prior Publication Data

US 2007/0055362 A1  Mar. 8, 2007

(51) Int. Cl.
*A61F 2/06* (2006.01)

(52) U.S. Cl. .................................... 623/1.35; 623/1.44

(58) Field of Classification Search .................. 623/1.44, 623/1.35, 1.15, 1.13, 1.32, 1.16
See application file for complete search history.

(56) References Cited

U.S. PATENT DOCUMENTS

| | | | |
|---|---|---|---|
| 4,309,994 A | 1/1982 | Grunwald | 128/214 R |
| 4,580,568 A | 4/1986 | Gianturco | 128/345 |
| 4,744,366 A | 5/1988 | Jang | 606/194 |
| 4,769,005 A | 9/1988 | Ginsburg et al. | 604/53 |
| 4,774,949 A | 10/1988 | Fogarty | 128/348.1 |
| 4,799,479 A | 1/1989 | Spears | 128/303.1 |
| 4,896,670 A | 1/1990 | Crittenden | 606/194 |
| 4,905,667 A | 3/1990 | Foerster et al. | 128/4 |
| 4,994,071 A | 2/1991 | MacGregor | 606/194 |
| 5,059,166 A | 10/1991 | Fischell et al. | 600/3 |
| 5,064,435 A | 11/1991 | Porter | 623/12 |
| 5,160,342 A | 11/1992 | Reger et al. | 606/200 |
| 5,342,387 A | 8/1994 | Summers | 606/198 |
| 5,383,892 A | 1/1995 | Cardon et al. | 606/198 |
| 5,387,235 A | 2/1995 | Chuter | 623/1 |
| 5,443,511 A | 8/1995 | Ogawa et al. | 623/16 |
| 5,449,373 A | 9/1995 | Pinchasik et al. | 606/198 |
| 5,456,712 A | 10/1995 | Maginot | 623/1 |
| 5,476,471 A | 12/1995 | Shifrin et al. | 606/151 |
| 5,487,730 A | 1/1996 | Marcadis et al. | 604/96 |
| 5,591,228 A | 1/1997 | Edoga | 623/1 |
| 5,607,444 A | 3/1997 | Lam | 606/194 |

(Continued)

FOREIGN PATENT DOCUMENTS

CA   2220864   7/1999

(Continued)

OTHER PUBLICATIONS

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

(Continued)

*Primary Examiner* — Corrine M McDermott
*Assistant Examiner* — Melissa Ryckman
(74) *Attorney, Agent, or Firm* — Vidas, Arrett & Steinkraus, P.A.

(57) ABSTRACT

A medical device may comprise a body portion and an outwardly deployable side branch structure, and may be formed from a first stent and a second stent. In some embodiments, the first stent and second stent may be connected by at least one connection. At least a portion of the second stent may be oriented within the first stent and may be coaxially aligned with the first stent. Either stent may include the side branch structure, and the stent not having side branch structure may include a side branch opening. The first and second stents may overlap at various locations to provide additional vessel support.

20 Claims, 12 Drawing Sheets

U.S. PATENT DOCUMENTS

| | | | |
|---|---|---|---|
| 5,607,445 A | 3/1997 | Summers | 623/1.22 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,618,299 A | 4/1997 | Khosravi et al. | 606/198 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |
| 5,645,559 A | 7/1997 | Hachtman et al. | 606/198 |
| 5,667,523 A | 9/1997 | Bynon et al. | 606/198 |
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,690,670 A | 11/1997 | Davidson | 606/198 |
| 5,693,085 A | 12/1997 | Buirge et al. | 623/1 |
| 5,697,971 A | 12/1997 | Fischell et al. | 623/1 |
| 5,707,348 A | 1/1998 | Krogh | 602/41 |
| 5,709,713 A | 1/1998 | Evans et al. | 623/1 |
| 5,718,724 A | 2/1998 | Goicoechea et al. | 623/1 |
| 5,720,735 A | 2/1998 | Dorros | 604/284 |
| 5,722,984 A | 3/1998 | Fischell et al. | 606/198 |
| 5,723,004 A | 3/1998 | Dereume et al. | 623/1 |
| 5,733,303 A | 3/1998 | Israel et al. | 606/198 |
| 5,741,246 A | 4/1998 | Prescott | 606/7 |
| 5,746,765 A | 5/1998 | Kleshinski et al. | 606/198 |
| 5,749,825 A | 5/1998 | Fischell | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,770 A | 5/1998 | Ravenscroft | 623/1 |
| 5,755,771 A | 5/1998 | Penn et al. | 623/1 |
| 5,755,773 A | 5/1998 | Evans et al. | 623/1 |
| 5,755,778 A * | 5/1998 | Kleshinski | 623/1.13 |
| 5,782,906 A | 7/1998 | Marshall et al. | 623/1 |
| 5,800,507 A | 9/1998 | Schwartz | 623/1 |
| 5,800,525 A | 9/1998 | Bachinski et al. | 623/1 |
| 5,807,398 A | 9/1998 | Shaknovich | 623/1.11 |
| 5,807,404 A | 9/1998 | Richter | 623/1 |
| 5,820,595 A | 10/1998 | Parodi | 604/101.05 |
| 5,824,036 A | 10/1998 | Lauterjung | 623/1 |
| 5,824,040 A | 10/1998 | Cox et al. | 623/1 |
| 5,824,046 A | 10/1998 | Smith et al. | 623/1 |
| 5,824,052 A | 10/1998 | Khosravi et al. | 623/1.1 |
| 5,824,054 A | 10/1998 | Khosravi et al. | 623/1.44 |
| 5,827,320 A | 10/1998 | Richter et al. | 606/194 |
| 5,833,593 A | 11/1998 | Liprie | 600/3 |
| 5,833,694 A | 11/1998 | Poncet | 606/108 |
| 5,836,896 A | 11/1998 | Rosenschein | 601/2 |
| RE35,988 E | 12/1998 | Winston et al. | 623/1 |
| 5,843,168 A | 12/1998 | Dang | 623/1 |
| 5,851,464 A | 12/1998 | Davila et al. | 264/103 |
| 5,853,419 A | 12/1998 | Imran | 606/1.15 |
| 5,861,168 A | 1/1999 | Cooke et al. | 424/424 |
| 5,868,777 A | 2/1999 | Lam | 606/194 |
| 5,871,437 A | 2/1999 | Alt | 600/3 |
| 5,879,381 A | 3/1999 | Moriuchi et al. | 623/1 |
| 5,893,887 A | 4/1999 | Jayaraman | 623/1 |
| 5,906,640 A | 5/1999 | Penn et al. | 623/1 |
| 5,916,264 A | 6/1999 | Von Oepen et al. | 623/1.15 |
| 5,919,126 A | 7/1999 | Armini | 600/3 |
| 5,938,682 A | 8/1999 | Hojeibane et al. | 606/198 |
| 5,938,697 A | 8/1999 | Killion et al. | 623/1 |
| 5,941,869 A | 8/1999 | Patterson et al. | 604/508 |
| 5,957,930 A | 9/1999 | Vrba | 606/108 |
| 5,961,548 A | 10/1999 | Shmulewitz | 623/1 |
| 5,972,017 A | 10/1999 | Berg et al. | 606/198 |
| 5,972,018 A | 10/1999 | Israel et al. | 606/198 |
| 5,976,181 A | 11/1999 | Whelan et al. | 623/1.12 |
| 5,976,182 A | 11/1999 | Cox | 623/1 |
| 5,980,565 A | 11/1999 | Jayaraman | 623/1 |
| 6,007,573 A | 12/1999 | Wallace et al. | 623/1 |
| 6,010,480 A | 1/2000 | Abele et al. | 604/96 |
| 6,013,054 A | 1/2000 | Jiun Yan | 604/96 |
| 6,015,433 A | 1/2000 | Roth | 623/1 |
| 6,017,324 A | 1/2000 | Tu et al. | 604/96 |
| 6,017,363 A * | 1/2000 | Hojeibane | 623/23.7 |
| 6,027,519 A | 2/2000 | Stanford | 606/198 |
| 6,030,414 A | 2/2000 | Taheri | 623/1 |
| 6,033,433 A | 3/2000 | Ehr et al. | 623/1 |
| 6,033,434 A | 3/2000 | Borghi | 623/1 |
| 6,033,435 A | 3/2000 | Penn et al. | 623/1 |
| 6,036,725 A | 3/2000 | Avellanet | 623/1.13 |
| 6,042,597 A | 3/2000 | Kveen et al. | 606/198 |
| 6,051,020 A | 4/2000 | Goicoechea et al. | 623/1 |
| 6,056,775 A | 5/2000 | Borghi et al. | 623/1.16 |
| 6,059,810 A | 5/2000 | Brown et al. | 606/198 |
| 6,059,824 A | 5/2000 | Taheri | 623/1 |
| 6,063,111 A | 5/2000 | Hieshima | 623/1.22 |
| 6,066,167 A | 5/2000 | Lau et al. | 623/1 |
| 6,068,655 A | 5/2000 | Seguin et al. | 623/1 |
| 6,074,659 A | 6/2000 | Kunz et al. | 424/423 |
| 6,077,413 A | 6/2000 | Hafeli et al. | 205/170 |
| 6,086,611 A | 7/2000 | Duffy et al. | 623/1 |
| 6,090,136 A | 7/2000 | McDonald et al. | 623/1.23 |
| 6,093,203 A | 7/2000 | Uflacker | 612/1.12 |
| 6,096,073 A | 8/2000 | Webster et al. | 612/1.16 |
| 6,099,455 A | 8/2000 | Columbo et al. | 600/3 |
| 6,099,497 A | 8/2000 | Adams et al. | 604/96.01 |
| 6,099,559 A | 8/2000 | Nolting | 623/1.16 |
| 6,113,579 A | 9/2000 | Eidenschink et al. | 604/264 |
| 6,113,628 A | 9/2000 | Borghi | 623/1.016 |
| 6,117,117 A | 9/2000 | Mauch | 604/284 |
| 6,117,156 A | 9/2000 | Richter et al. | 606/194 |
| 6,120,522 A | 9/2000 | Vrba et al. | 606/190 |
| 6,120,535 A | 9/2000 | McDonald et al. | 623/1.39 |
| 6,120,847 A | 9/2000 | Yang et al. | 427/335 |
| 6,123,712 A | 9/2000 | Di Caprio et al. | 606/108 |
| 6,123,723 A | 9/2000 | Konya et al. | 623/1.11 |
| 6,129,658 A | 10/2000 | Delfino et al. | 600/3 |
| 6,129,738 A | 10/2000 | Lashinski et al. | 606/194 |
| 6,131,266 A | 10/2000 | Saunders | 29/557 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,190,403 B1 | 2/2001 | Fischell et al. | 623/1 |
| 6,203,568 B1 | 3/2001 | Lombardi et al. | 623/1.13 |
| 6,210,380 B1 | 4/2001 | Mauch | 604/284 |
| 6,210,429 B1 | 4/2001 | Vardi et al. | 623/1.11 |
| 6,210,433 B1 | 4/2001 | Larre | 623/1.15 |
| 6,224,609 B1 | 5/2001 | Ressemann et al. | 606/108 |
| 6,231,598 B1 | 5/2001 | Berry et al. | 623/1.15 |
| 6,245,100 B1 | 6/2001 | Davila et al. | 623/1.13 |
| 6,253,769 B1 | 7/2001 | LaFontaine et al. | 128/898 |
| 6,254,593 B1 | 7/2001 | Wilson | 606/1.11 |
| 6,254,628 B1 | 7/2001 | Wallace et al. | 623/1.12 |
| 6,258,115 B1 | 7/2001 | Dubrul | 606/200 |
| 6,258,116 B1 | 7/2001 | Hojeibane | 623/1.16 |
| 6,258,117 B1 | 7/2001 | Camrud et al. | 623/1.16 |
| 6,261,305 B1 | 7/2001 | Marotta et al. | 606/200 |
| 6,261,316 B1 | 7/2001 | Shaolian et al. | 623/1.11 |
| 6,261,319 B1 | 7/2001 | Kveen et al. | 623/1.15 |
| 6,261,320 B1 | 7/2001 | Tam et al. | 623/1.15 |
| 6,264,662 B1 | 7/2001 | Lauterjung | 606/108 |
| 6,264,682 B1 | 7/2001 | Wilson et al. | 623/1 |
| 6,264,686 B1 | 7/2001 | Rieu et al. | 623/1.16 |
| 6,290,673 B1 | 9/2001 | Shanley | 604/102.02 |
| 6,290,720 B1 | 9/2001 | Khosravi et al. | 623/1.13 |
| 6,293,968 B1 | 9/2001 | Taheri | 623/1.15 |
| 6,302,906 B1 | 10/2001 | Goicoechea et al. | 623/1.11 |
| 6,312,460 B2 | 11/2001 | Drasler et al. | 623/1.15 |
| 6,312,463 B1 | 11/2001 | Rourke et al. | 623/1.39 |
| 6,325,820 B1 | 12/2001 | Khosravi et al. | 623/1.13 |
| 6,325,821 B1 | 12/2001 | Gaschino et al. | 623/1.15 |
| 6,325,823 B1 | 12/2001 | Horzewski et al. | 623/1.16 |
| 6,325,825 B1 | 12/2001 | Kula et al. | 623/1.3 |
| 6,325,826 B1 | 12/2001 | Vardi et al. | 623/1.35 |
| 6,331,191 B1 | 12/2001 | Chobotov | 623/1.44 |
| 6,334,864 B1 | 1/2002 | Amplatz et al. | 606/200 |
| 6,334,870 B1 | 1/2002 | Ehr et al. | 623/1.16 |
| 6,346,089 B1 | 2/2002 | Dibie | 603/1.15 |
| 6,355,059 B1 | 3/2002 | Richter et al. | 623/1.17 |
| 6,355,060 B1 | 3/2002 | Lenker et al. | 623/1.34 |

| | | | | |
|---|---|---|---|---|
| 6,361,544 B1 | 3/2002 | Wilson et al. ............... 606/194 |
| 6,361,555 B1 | 3/2002 | Wilson ............................ 623/1.11 |
| 6,383,213 B2 | 5/2002 | Wilson et al. ................. 623/1.11 |
| 6,395,018 B1 | 5/2002 | Castaneda ..................... 623/1.13 |
| 6,428,569 B1 | 8/2002 | Brown ........................... 623/1.15 |
| 6,436,104 B2 | 8/2002 | Hojeibane ...................... 606/108 |
| 6,436,134 B2 | 8/2002 | Richter et al. ................. 623/1.15 |
| 6,443,971 B1 | 9/2002 | Boylan et al. ................. 606/200 |
| 6,451,049 B2 | 9/2002 | Vallana et al. ................. 623/1.15 |
| 6,478,816 B1 | 11/2002 | Kveen et al. .................. 623/1.15 |
| 6,485,509 B2 | 11/2002 | Killion et al. ................. 623/1.15 |
| 6,488,703 B1 | 12/2002 | Kveen et al. .................. 623/1.15 |
| 6,491,619 B1 | 12/2002 | Trauthen et al. ................ 600/3 |
| 6,506,211 B1 | 1/2003 | Skubitz et al. ................. 623/1.15 |
| 6,508,836 B2 | 1/2003 | Wilson et al. ................. 623/1.35 |
| 6,514,228 B1 | 2/2003 | Hamilton et al. ........... 604/96.01 |
| 6,517,515 B1 | 2/2003 | Eidenschink ............ 604/101.05 |
| 6,517,558 B2 | 2/2003 | Gittings et al. ............... 606/153 |
| 6,520,988 B1 | 2/2003 | Colombo et al. ............. 623/1.35 |
| 6,540,779 B2 | 4/2003 | Richter et al. ............... 623/1.35 |
| 6,562,067 B2 | 5/2003 | Mathis .......................... 623/1.16 |
| 6,579,309 B1 | 6/2003 | Loos et al. ..................... 623/1.16 |
| 6,579,312 B2 | 6/2003 | Wilson et al. ................. 623/1.35 |
| 6,582,394 B1 | 6/2003 | Reiss et al. ................. 604/96.01 |
| 6,596,020 B2 | 7/2003 | Vardi et al. .................... 623/1.11 |
| 6,599,316 B2 | 7/2003 | Vardi et al. .................... 623/1.15 |
| 6,623,240 B2 | 9/2003 | Ertl et al. ........................ 415/163 |
| 6,645,242 B1 | 11/2003 | Quinn ........................... 623/1.16 |
| 6,669,723 B2 | 12/2003 | Killion et al. ................. 623/1.15 |
| 6,676,701 B2 | 1/2004 | Rourke et al. ................. 623/1.39 |
| 6,689,156 B1 | 2/2004 | Davidson et al. ............. 623/1.11 |
| 6,692,483 B2 | 2/2004 | Vardi et al. .................... 604/529 |
| 6,695,833 B1* | 2/2004 | Frantzen ........................ 623/1.13 |
| 6,695,877 B2 | 2/2004 | Brucker et al. ................ 623/1.16 |
| 6,706,062 B2 | 3/2004 | Vardi et al. .................... 623/1.35 |
| 6,712,844 B2 | 3/2004 | Pacetti ........................... 623/1.15 |
| 6,749,628 B1 | 6/2004 | Callol et al. .................. 623/1.15 |
| 6,752,825 B2 | 6/2004 | Eskuri ............................ 623/1.12 |
| 6,776,793 B2 | 8/2004 | Brown et al. ................. 623/1.15 |
| 6,811,566 B1 | 11/2004 | Penn et al. .................... 623/1.15 |
| 6,835,203 B1 | 12/2004 | Vardi et al. .................... 623/1.34 |
| 6,858,038 B2 | 2/2005 | Heuser .......................... 623/1.35 |
| 6,884,258 B2 | 4/2005 | Vardi et al. .................... 623/1.11 |
| 6,896,699 B2 | 5/2005 | Wilson et al. ................. 623/1.35 |
| 6,932,837 B2 | 8/2005 | Amplatz et al. ............... 623/1.15 |
| 6,955,687 B2 | 10/2005 | Richter et al. ................. 623/1.35 |
| 6,955,688 B2 | 10/2005 | Wilson et al. ................. 623/1.35 |
| 6,962,602 B2 | 11/2005 | Vardi et al. .................... 623/1.11 |
| 7,018,400 B2 | 3/2006 | Lashinski et al. ............. 623/1.11 |
| 7,056,323 B2 | 6/2006 | Mareiro et al. ............... 606/108 |
| 7,060,091 B2 | 6/2006 | Killion et al. ................. 623/1.15 |
| 2001/0003161 A1 | 6/2001 | Vardi et al. .................... 623/1.11 |
| 2001/0004706 A1 | 6/2001 | Hojeibane ...................... 623/1.11 |
| 2001/0004707 A1 | 6/2001 | Dereurne et al. .............. 623/1.16 |
| 2001/0012927 A1 | 8/2001 | Mauch .......................... 604/284 |
| 2001/0016766 A1 | 8/2001 | Vardi et al. .................... 623/1.11 |
| 2001/0016767 A1 | 8/2001 | Wilson et al. ................. 623/1.11 |
| 2001/0016768 A1 | 8/2001 | Wilson et al. ................. 623/1.11 |
| 2001/0025195 A1 | 9/2001 | Shaolian et al. ............... 623/1.13 |
| 2001/0027291 A1 | 10/2001 | Shanley ......................... 604/104 |
| 2001/0027338 A1 | 10/2001 | Greenberg ..................... 623/1.13 |
| 2001/0029396 A1 | 10/2001 | Wilson et al. ................. 623/1.11 |
| 2001/0037116 A1 | 11/2001 | Wilson et al. ................. 606/108 |
| 2001/0037138 A1 | 11/2001 | Wilson et al. ................. 623/1.11 |
| 2001/0039448 A1 | 11/2001 | Dibie ............................. 623/1.16 |
| 2001/0044649 A1 | 11/2001 | Vallana et al. ................. 623/1.15 |
| 2001/0044650 A1 | 11/2001 | Simso et al. ................... 623/1.15 |
| 2001/0049552 A1 | 12/2001 | Richter et al. ................. 623/1.15 |
| 2001/0056297 A1 | 12/2001 | Hojeibane ...................... 623/1.16 |
| 2002/0013618 A1 | 1/2002 | Marotta et al. ................ 623/1.15 |
| 2002/0013619 A1 | 1/2002 | Shanley ......................... 623/1.15 |
| 2002/0022874 A1 | 2/2002 | Wilson ........................... 623/1.11 |
| 2002/0026232 A1 | 2/2002 | Marotta et al. ................ 623/1.16 |
| 2002/0035392 A1 | 3/2002 | Wilson ........................... 623/1.11 |
| 2002/0042650 A1 | 4/2002 | Vardi et al. .................... 623/1.35 |
| 2002/0052648 A1 | 5/2002 | McGuckin, Jr. et al. .... 623/1.35 |
| 2002/0068969 A1 | 6/2002 | Shanley et al. ................ 623/1.16 |
| 2002/0072790 A1 | 6/2002 | McGuckin, Jr. et al. .... 623/1.12 |
| 2002/0111675 A1 | 8/2002 | Wilson ........................... 623/1.35 |
| 2002/0116046 A1 | 8/2002 | DeCaprio ....................... 623/1.11 |
| 2002/0156516 A1 | 10/2002 | Vardi et al. .................... 623/1.11 |
| 2002/0156517 A1 | 10/2002 | Perouse ......................... 623/1.11 |
| 2002/0165604 A1 | 11/2002 | Shanley ......................... 623/1.15 |
| 2002/0173835 A1 | 11/2002 | Bourang et al. ............... 623/1.11 |
| 2002/0173840 A1 | 11/2002 | Brucker et al. ................ 623/1.16 |
| 2002/0183763 A1 | 12/2002 | Callol et al. .................. 606/108 |
| 2002/0193872 A1 | 12/2002 | Trout, III et al. .............. 623/1.34 |
| 2002/0193873 A1 | 12/2002 | Brucker et al. ................ 623/1.35 |
| 2003/0009209 A1 | 1/2003 | Hojeibane ...................... 623/1.11 |
| 2003/0028233 A1 | 2/2003 | Vardi et al. .................... 623/1.11 |
| 2003/0050688 A1 | 3/2003 | Fischell et al. ................ 623/1.15 |
| 2003/0055378 A1 | 3/2003 | Wang et al. ............. 604/103.07 |
| 2003/0055483 A1 | 3/2003 | Gumm ........................... 623/1.11 |
| 2003/0074047 A1 | 4/2003 | Richter .......................... 623/1.11 |
| 2003/0093109 A1 | 5/2003 | Mauch ........................... 606/194 |
| 2003/0097169 A1 | 5/2003 | Brucker ......................... 623/1.11 |
| 2003/0114912 A1 | 6/2003 | Sequin et al. .................. 623/1.11 |
| 2003/0125791 A1 | 7/2003 | Sequin et al. .................. 623/1.11 |
| 2003/0125802 A1 | 7/2003 | Callol et al. .................. 623/1.35 |
| 2003/0135259 A1 | 7/2003 | Simso ............................ 623/1.12 |
| 2003/0181923 A1 | 9/2003 | Vardi .............................. 606/108 |
| 2003/0195606 A1 | 10/2003 | Davidson et al. ............. 623/1.11 |
| 2003/0204245 A1 | 10/2003 | Brightbill ....................... 623/1.16 |
| 2004/0006381 A1 | 1/2004 | Sequin et al. .................. 623/1.12 |
| 2004/0015227 A1* | 1/2004 | Vardi et al. .................... 623/1.16 |
| 2004/0034403 A1 | 2/2004 | Schmitt ......................... 623/1.2 |
| 2004/0044396 A1 | 3/2004 | Clerc et al. .................... 623/1.13 |
| 2004/0059406 A1 | 3/2004 | Cully et al. .................... 623/1.11 |
| 2004/0088007 A1 | 5/2004 | Eidenschink .................. 607/1 |
| 2004/0111142 A1 | 6/2004 | Rourke et al. ................. 623/1.1 |
| 2004/0117003 A1 | 6/2004 | Ouriel et al. ................... 623/1.35 |
| 2004/0133268 A1 | 7/2004 | Davidson et al. ............. 623/1.35 |
| 2004/0138732 A1 | 7/2004 | Suhr et al. ..................... 623/1.11 |
| 2004/0138737 A1 | 7/2004 | Davidson et al. ............. 623/1.35 |
| 2004/0148006 A1 | 7/2004 | Davidson et al. ............. 623/1.11 |
| 2004/0172121 A1 | 9/2004 | Eidenschink et al. ......... 623/1.11 |
| 2004/0186560 A1 | 9/2004 | Alt .................................. 623/1.35 |
| 2004/0225345 A1 | 11/2004 | Fischell et al. ................ 623/1.11 |
| 2004/0267352 A1 | 12/2004 | Davidson et al. ............. 623/1.15 |
| 2005/0004656 A1 | 1/2005 | Das ................................ 623/1.16 |
| 2005/0010278 A1 | 1/2005 | Vardi et al. .................... 623/1.35 |
| 2005/0015108 A1 | 1/2005 | Williams et al. .............. 606/194 |
| 2005/0015135 A1 | 1/2005 | Shanley ......................... 623/1.11 |
| 2005/0049674 A1 | 3/2005 | Berra et al. .................... 623/1.13 |
| 2005/0060027 A1 | 3/2005 | Khenansho et al. ........... 623/1.35 |
| 2005/0096726 A1 | 5/2005 | Sequin et al. .................. 623/1.12 |
| 2005/0102021 A1 | 5/2005 | Osborne ......................... 623/1.13 |
| 2005/0102023 A1 | 5/2005 | Yadin et al. .................... 623/1.15 |
| 2005/0107863 A1 | 5/2005 | Brown ........................... 623/1.15 |
| 2005/0119731 A1 | 6/2005 | Brucker et al. ................ 623/1.35 |
| 2005/0125076 A1 | 6/2005 | Ginn .............................. 623/23.65 |
| 2005/0131535 A1 | 6/2005 | Wong ............................. 623/1.15 |
| 2005/0149161 A1 | 7/2005 | Eidenschink et al. ......... 623/1.11 |
| 2005/0154442 A1 | 7/2005 | Eidenschink et al. ......... 623/1.11 |
| 2005/0154444 A1 | 7/2005 | Quadri ........................... 623/1.13 |
| 2005/0183259 A1 | 8/2005 | Eidenschink et al. ......... 29/508 |
| 2005/0209673 A1 | 9/2005 | Shaked .......................... 623/1.11 |
| 2005/0228483 A1 | 10/2005 | Kaplan et al. ................. 623/1.15 |
| 2005/0278017 A1 | 12/2005 | Gregorich ...................... 623/1.44 |
| 2006/0036315 A1 | 2/2006 | Yadin et al. .................... 623/1.35 |
| 2006/0041303 A1 | 2/2006 | Israel ............................. 623/1.11 |
| 2006/0079956 A1 | 4/2006 | Eigler et al. ................... 623/1.35 |
| 2006/0173528 A1 | 8/2006 | Feld et al. ...................... 623/1.15 |
| 2007/0050016 A1 | 3/2007 | Gregorich et al. |
| 2007/0073376 A1 | 3/2007 | Krolik et al. .................. 623/1.11 |

FOREIGN PATENT DOCUMENTS

| | | |
|---|---|---|
| DE | 9014845 | 2/1991 |
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0 878 173 B1 | 11/1997 |
| EP | 0804907 | 11/1997 |
| EP | 0479557 | 7/1998 |
| EP | 0 876 806 A1 | 11/1998 |
| EP | 0876805 | 11/1998 |

| | | |
|---|---|---|
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 95/31945 | 11/1995 |
| WO | 96/26696 | 9/1996 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/22045 | 5/1998 |
| WO | 98/32412 | 7/1998 |
| WO | 98/36709 | 8/1998 |
| WO | 98/37833 | 9/1998 |
| WO | 98/47447 | 10/1998 |
| WO | 98/48879 | 11/1998 |
| WO | 98/49964 | 11/1998 |
| WO | 98/53765 | 12/1998 |
| WO | 99/03426 | 1/1999 |
| WO | 99/04726 | 2/1999 |
| WO | 99/15103 | 4/1999 |
| WO | 99/15109 | 4/1999 |
| WO | 99/24104 | 5/1999 |
| WO | 99/30638 | 6/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 01/45594 | 6/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/53250 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |
| WO | 01/00112 A1 | 1/2001 |
| WO | 01/08600 | 2/2001 |
| WO | 01/21095 | 3/2001 |
| WO | 01/21109 | 3/2001 |
| WO | 01/21244 | 3/2001 |
| WO | 01/34064 A2 | 5/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/41829 A1 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/32347 | 4/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004021929 | 3/2004 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |

OTHER PUBLICATIONS

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, ""Kissing" Stent for Bifurcational Coronary Lesion," *Catheterization and Cardiovascular Diagnosis*, vol. 30, pp. 327-330 (Dec. 1993).

Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

U.S. Appl. No. 09/659,571, filed Sep. 12, 2000, Olson et al.
U.S. Appl. No. 11/138,022, filed May 26, 2005, Dan Gregorich, Michael P. Meyer.
U.S. Appl. No. 11/138,202, filed May 26, 2005, Michael P. Meyer; Daniel J. Gregorich; Kevin P. Grotheim.
U.S. Appl. No. 11/138,196, filed May 26, 2005, Daniel Gregorich, Michael Meyer.
U.S. Appl. No. 09/325,996, filed Jun. 4, 1999, Vardi et al.
U.S. Appl. No. 09/614,472, filed Jul. 11, 2000, Davidson et al.
U.S. Appl. No. 09/663,111, filed Sep. 15, 2000, Davidson et al.

* cited by examiner

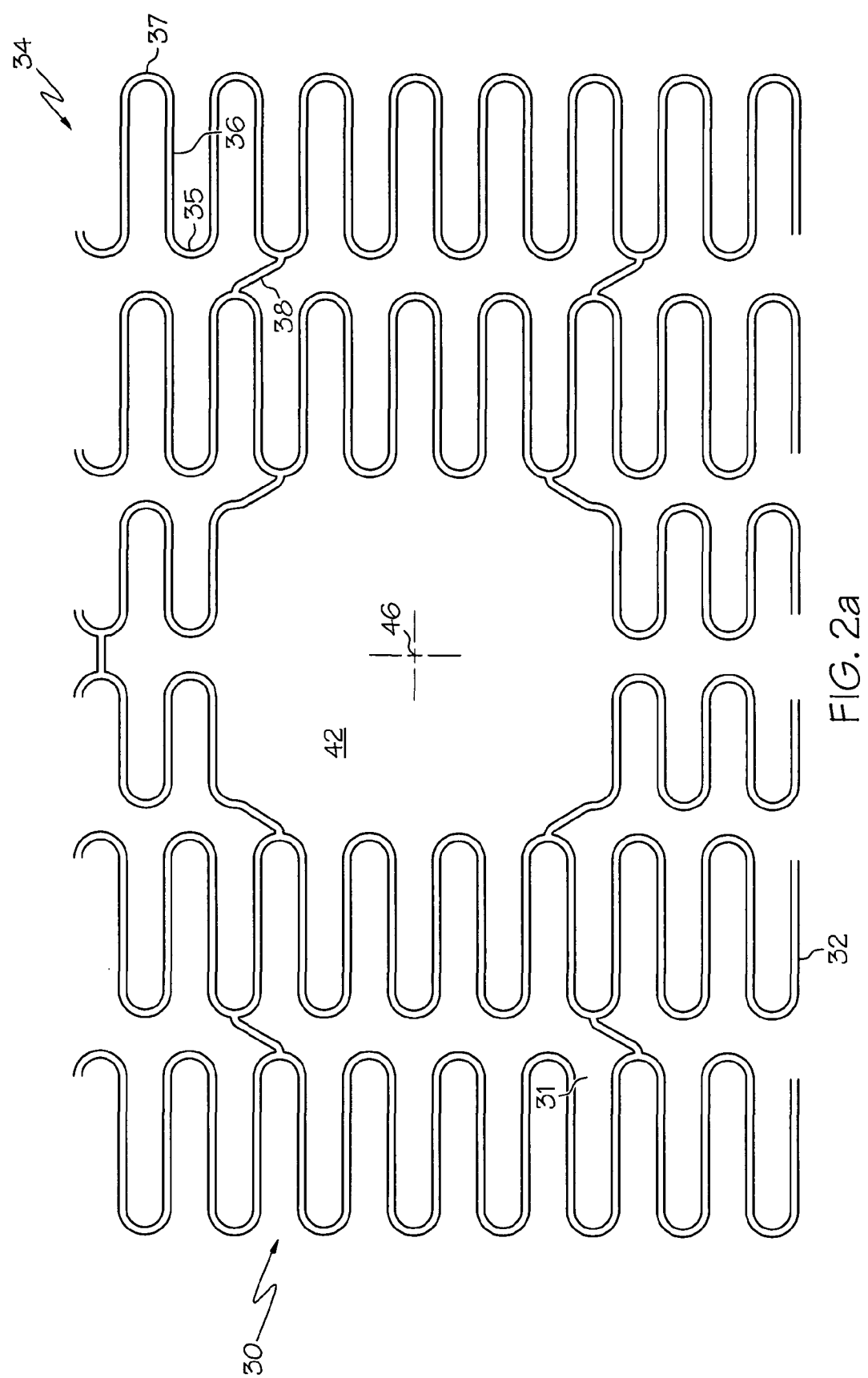

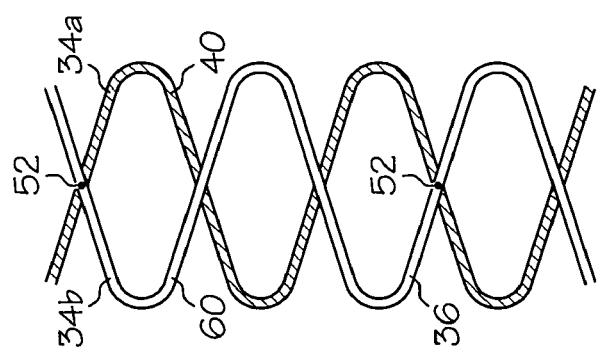

OVERLAPPING STENT

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

There remains a need for stents with innovative designs which combine excellent scaffolding support, compression resistance and side branch access.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a medical device comprising a first stent and a second stent, wherein at least a portion of the second stent is oriented within the first stent. The first and second stents are coaxially aligned and either the first stent or the second stent includes an outwardly deployable side branch structure. In some embodiments, the first stent and the second stent may be connected by at least one connection.

In at least one other embodiment, a medical device comprises a first stent and a second stent. The first stent comprises a plurality of interconnected struts, the struts defining a plurality of cells including a side branch opening. The side branch opening comprises a cell having a different shape than other cells of the stent. The second stent comprises a plurality of interconnected struts, the struts defining a plurality of cells and a side branch structure having an outwardly deployable petal. At least a portion of the second stent is disposed within the first stent.

In further embodiments, the invention is directed to an assembly comprising a delivery catheter and a medical device comprising a first stent and a second stent, wherein at least a portion of the second stent is coaxially oriented within the first stent. The medical device further comprises an outwardly deployable side branch structure. The medical device is oriented about a distal portion of the catheter.

In further embodiments, the invention is directed to a method of stenting a vessel comprising providing a delivery catheter having an expandable medical device oriented about a distal end. The medical device comprises a first stent and a second stent, at least a portion of the second stent oriented within the first stent and coaxially aligned with the first stent. The medical device further comprises an outwardly deployable side branch structure. The method further comprises delivering the medical device to a deployment location in a bodily vessel, and expanding the medical device.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 1 shows an embodiment of a medical device.

FIG. 2*a* shows an embodiment of stent structure suitable for use in a medical device.

FIG. 2*b* shows another embodiment of stent structure suitable for use in a medical device.

FIG. 2*c* shows a flat pattern for an embodiment of a medical device comprising the stent structures of FIGS. 2*a* and 2*b*.

DETAILED DESCRIPTION OF THE INVENTION

Figure 1:
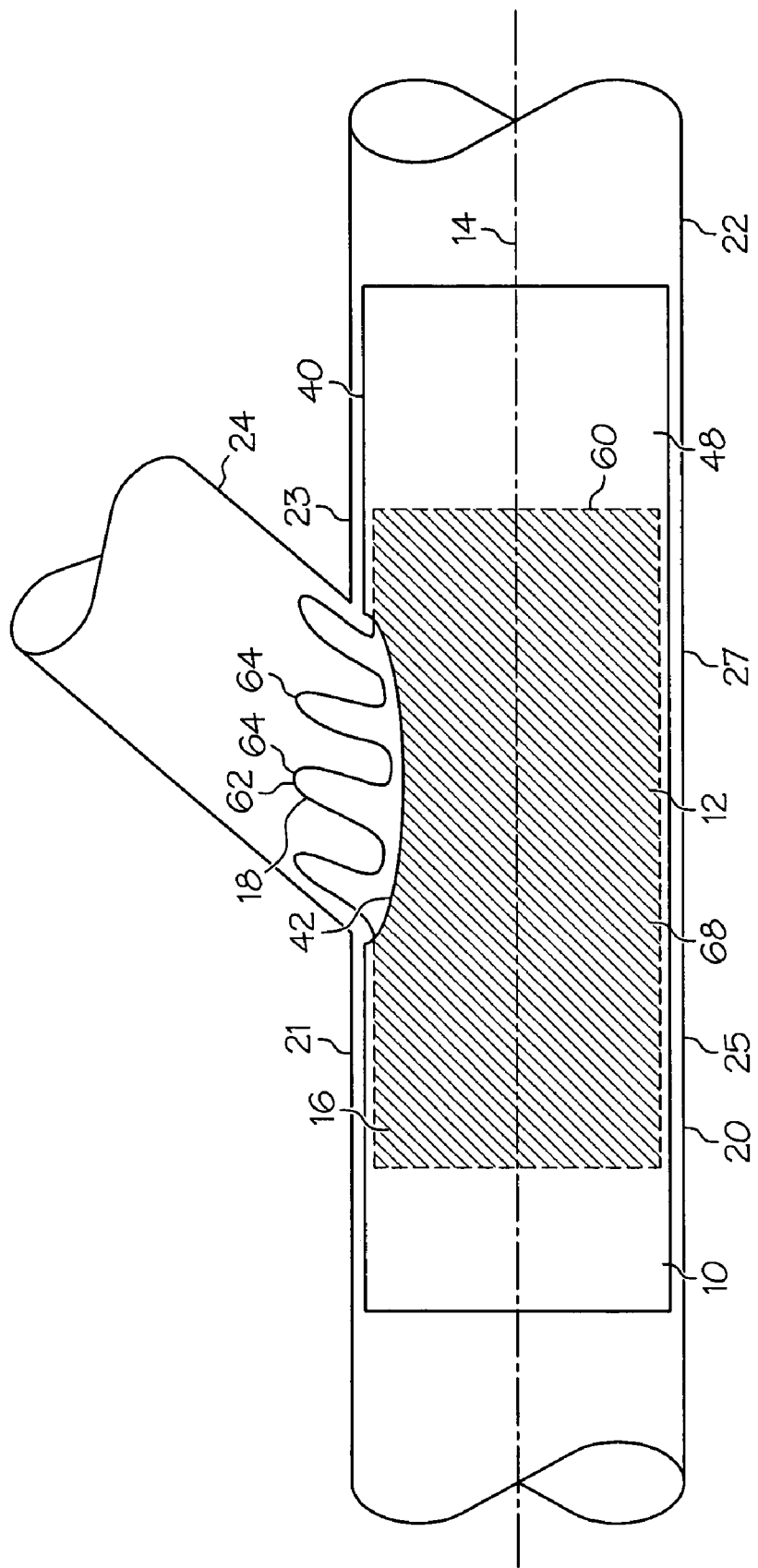

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIG. 1 shows an embodiment of a medical device 10 which may comprise a stent, graft, stent-graft or other structure suitable for use within a bodily vessel 20. The medical device 10 may comprise an expandable body portion 12 and an outwardly deployable side branch portion 18. The medical device 10 may be deployed within a vessel 20, for example with the body portion 12 oriented within a main branch vessel 22 and the side branch portion 18 deployed into a side branch vessel 24.

The medical device 10 may comprise a first stent 40 and a second stent 60. At least a portion of the second stent 60 may be oriented within the first stent 40. The stents 40, 60 may be coaxially aligned about a common longitudinal axis 14. Thus, a central axis of the first stent 40 and a central axis of the second stent 60 may be collinear. Each stent may comprise any suitable stent framework pattern. In various embodiments, other suitable devices such as grafts, stent-grafts, etc., may be substituted for the traditional stent framework of a first stent 40 and/or a second stent 60.

In some embodiments, one of the stents 40, 60 may comprise a side branch opening, and one of the stents 40, 60 may comprise a side branch structure having outwardly deployable petals 64. As depicted in FIG. 1, the first or outer stent 40 includes a side branch opening 42 which is free of structural struts. The second or inner stent 60 includes side branch structure 62 having a plurality of outwardly deployable petals 64. When the inner stent 60 includes side branch structure 62, portions of the side branch structure 62 may deploy outwardly through the side branch opening 42 of the outer stent 40.

The stents 40, 60 may include body portions 48, 68 which may each comprise a plurality of interconnected struts. Individually, the interconnected struts of either stent 40, 60 may provide a respective amount of vessel support. Areas of the medical device 10 where the individual strut patterns overlap 16, such as indicated by the shaded region in FIG. 1, desirably provide increased vessel coverage and support.

Various embodiments of a medical device 10 may be arranged to provide overlap 16 and greater vessel support at a number of areas near a vessel 20 bifurcation, such as an area 21 adjacent to the ostium near the contralateral ostial wall, an area 23 adjacent to the ostium near the carina, an area 25 opposite the ostium and contralateral ostial wall, and an area 27 opposite the ostium and carina.

FIG. 2a shows an embodiment of a flat pattern for a stent 30 which may be suitable for use as either a first stent 40 or a second stent 60 in a medical device 10. The stent 30 may comprise a plurality of interconnected struts 32. Areas between the interconnected struts 32 may comprise cells 31.

The stent 30 may include a plurality of serpentine bands 34 which may extend about the circumference of the stent 30. Each serpentine band 34 may comprise a plurality of band struts 36 connected by alternating proximal turns 35 and distal turns 37. In some embodiments, the band struts 36 may be straight along their length. Adjacent serpentine bands 34 may be connected by connector struts 38.

The stent 30 may further comprise a side branch opening 42, which may comprise a side branch cell having a shape that is different from other cells 31 of the stent 30. In some embodiments, a side branch opening 42 may be symmetrical about its center 46.

Figure 2B:
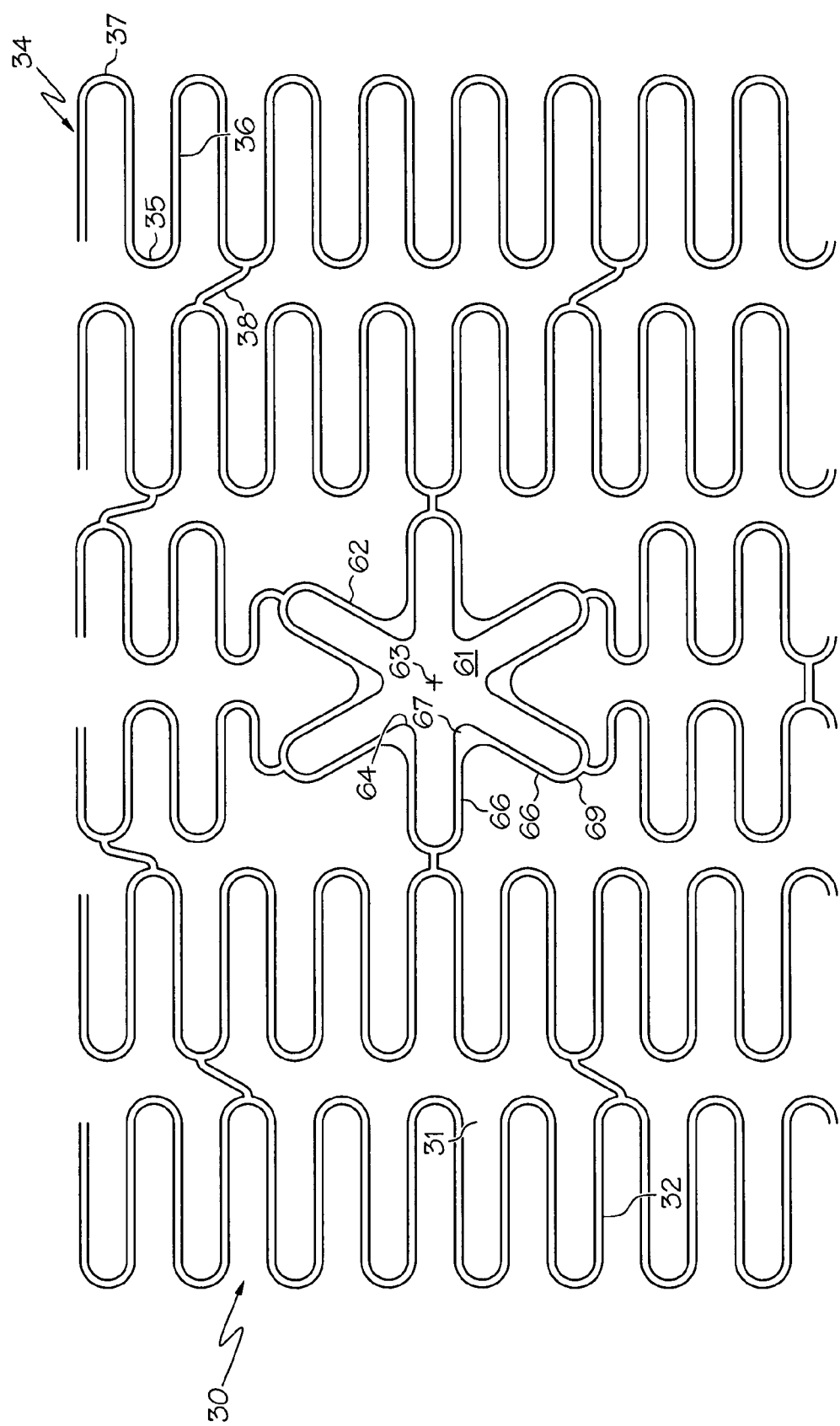
FIG. 2d shows a portion of a medical device after expansion.
FIG. 2e shows another flat pattern for an embodiment of a medical device comprising the stent structures of FIGS. 2a and 2b.

FIG. 2b shows another embodiment of a flat pattern for a stent 30 which may be suitable for use as either a first stent 40 or a second stent 60 in a medical device 10. The stent 30 may comprise interconnected struts 32 arranged to form cells 31, serpentine bands 34 and connector struts 38, for example as described with respect to the stent 30 of FIG. 2a.

The stent 30 may further comprise a side branch structure 62 which may comprise a continuous strut member, or in some embodiments a plurality of strut members, which may extend in a generally serpentine fashion about the center 63 of the side branch structure 62. While "serpentine" may be used describe most embodiments, the term is not intended to limit the invention. The side branch structure 62 may have any suitable size, shape and configuration of struts.

In some embodiments, the side branch structure 62 may define a plurality of side branch petals 64 which may have any suitable shape and may each be oriented in any suitable direction. A cell 61 of the side branch structure 62 may be different than any other cell 31 of the stent 30.

Each petal 64 may comprise a plurality of struts 66 and at least one turn 67. A strut 66 may be straight along its length, and may be oriented in any suitable direction. A turn 67 may be oriented in any suitable direction and in some embodiments may be oriented toward the center 63 of the side branch cell 61. Petals 64 which are adjacent to one another about the side branch structure 62 may be connected to one another by a connecting portion 69.

Figure 2C:
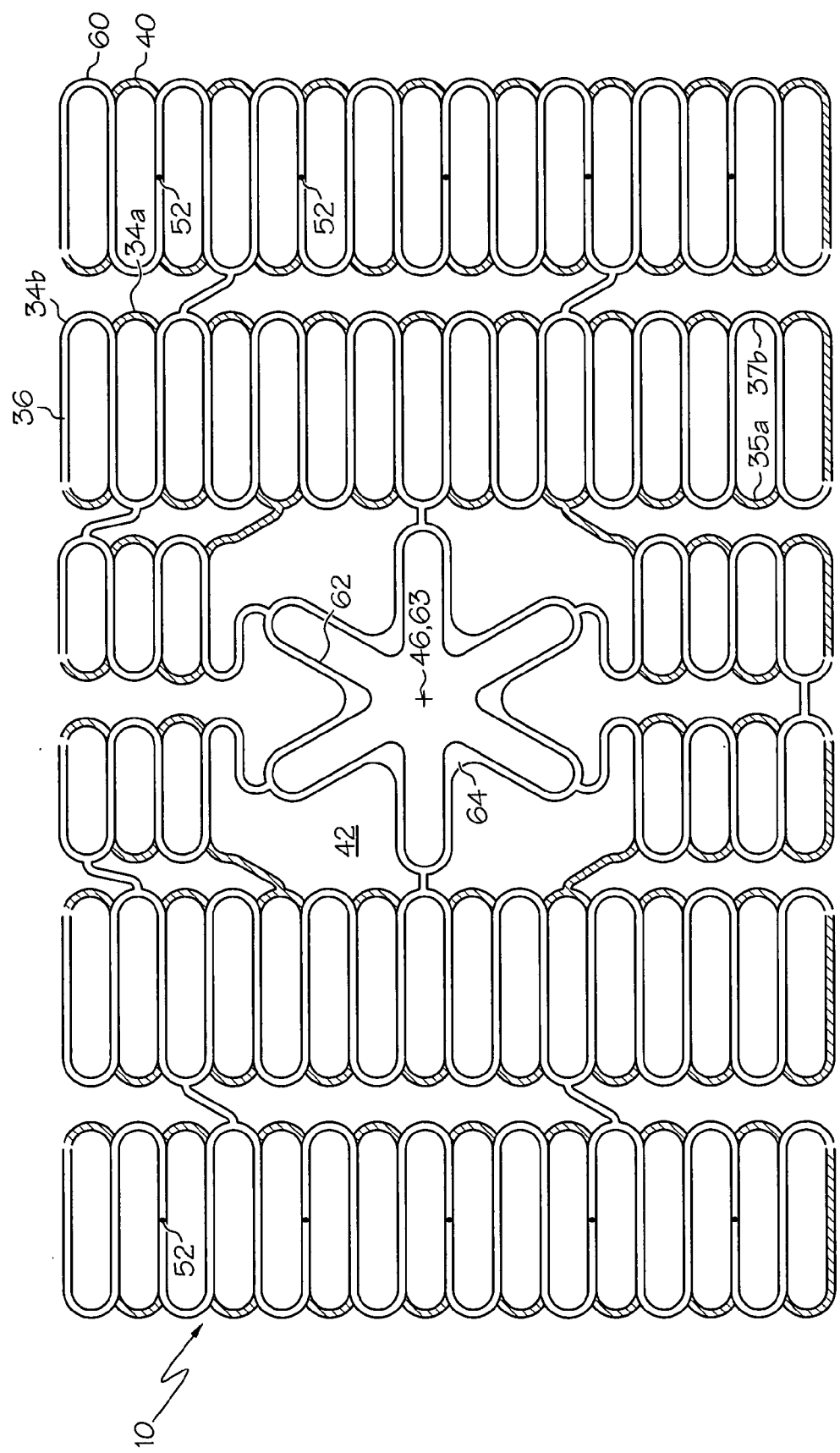

FIG. 2c shows an embodiment of a flat pattern for a medical device 10 comprising a first stent 40 and a second stent 60. A person of ordinary skill in the art will recognize that the flat pattern may be rolled to form a cylindrical medical device 10, and that rolling the flat pattern in one direction may produce a medical device 10 wherein the first stent 40 comprises an outer stent, whereas rolling the flat pattern in the opposite direction may produce a medical device 10 wherein the first stent 40 comprises an inner stent.

As depicted, the flat pattern for the second stent 60 may be positioned over the flat pattern for the first stent 40. The second stent 60 may comprise a stent pattern as depicted in FIG. 2b having a side branch structure 62 including a plurality of petals 64. The first stent 40 may comprise a stent pattern as depicted in FIG. 2a having a side branch opening 42. The stents 40, 60 may be oriented such that the center 46 of the side branch opening 42 of the first stent 40 is aligned with the center 63 of the side branch structure 62 of the second stent 60.

In some embodiments, the first stent 40 may be connected to the second stent 60 by at least one and in some embodiments a plurality of connections 52. A connection 52 may be located on any suitable area of the medical device 10. A connection 52 may comprise any suitable connection between the stents 40, 60. In some embodiments, a connection 52 may comprise a welded, brazed or soldered connection, an adhesive connection, an encapsulated connection, a suture, ring, collar or band, rivets or pins, cooperative tabs and/or notches, friction pads, hook and loop fasteners, etc. In some embodiments, connections 52 may be insulated, wherein conductivity across the connection 52 is minimized, for example to enhance MRI compatibility.

Desirably, the orientation of the stent patterns 40, 60 and the locations of the connections 52 allow the medical device 10 to provide greater vessel support than either stent 40, 60 individually.

The serpentine bands 34a of the first stent 40 may be staggered or offset from the serpentine bands 34b of the second stent 60 in a direction about the circumference of the medical device 10. Thus, a proximal turn 35a of the first stent 40 may be aligned with a distal turn 37b of the second stent 60 in a longitudinal direction of the medical device 10.

Connections 52 between the stents 40, 60 may be located along band struts 36 of the serpentine bands 34. In some embodiments, the connections 52 may be located at the midpoint of a band strut 36.

Medical devices 10 may be delivered to a deployment site using any suitable stent delivery system. In some embodiments, the first stent 40 and the second stent 60 may be delivered and deployed while maintaining a coaxial orientation. In some embodiments, a first stent 40 and a second stent 60 may be delivered to the deployment site separately or independently of one another. For example, the first stent 40 may be delivered to the deployment site, properly oriented and expanded. The second stent 60 may then be delivered to the deployment site, oriented coaxially within the first stent 40 and expanded.

FIG. 2d shows a portion of a medical device according to FIG. 2c after expansion. The staggered orientation of the serpentine bands 34a, 34b of the first stent 40 and the second stent 60, and the locations of the connections 52, provide greater vessel support than either stent 40, 60 individually. It is also clear from FIG. 2d that at least a portion of the interconnected strut pattern of the first stent 40 may comprise a mirror image of a portion of the interconnected strut pattern of the second stent 60.

In some embodiments, it is desirable for portions of the stents 40, 60 to have similar expansion characteristics, such as change in diameter, change in length, etc. For example, the serpentine bands 34 of the stents 40, 60 are similarly shaped, and will experience a substantially equal amount of diameter increase and a substantially equal amount of size change along the length of the medical device during expansion.

Desirably, a line oriented in a radial direction of the medical device 10 in some locations may pass through a cell 31 of the second stent 60 and intersect a strut 32 of the first stent 40. In some other locations, a radial line may pass through a cell 31 of the first stent 40 and intersect a strut 32 of the second stent 60. In other locations, a radial line may pass through cells 31 of both stents 40, 60. In still other locations, a radial line may intersect struts 32 of both stents 40, 60.

Figure 2E:
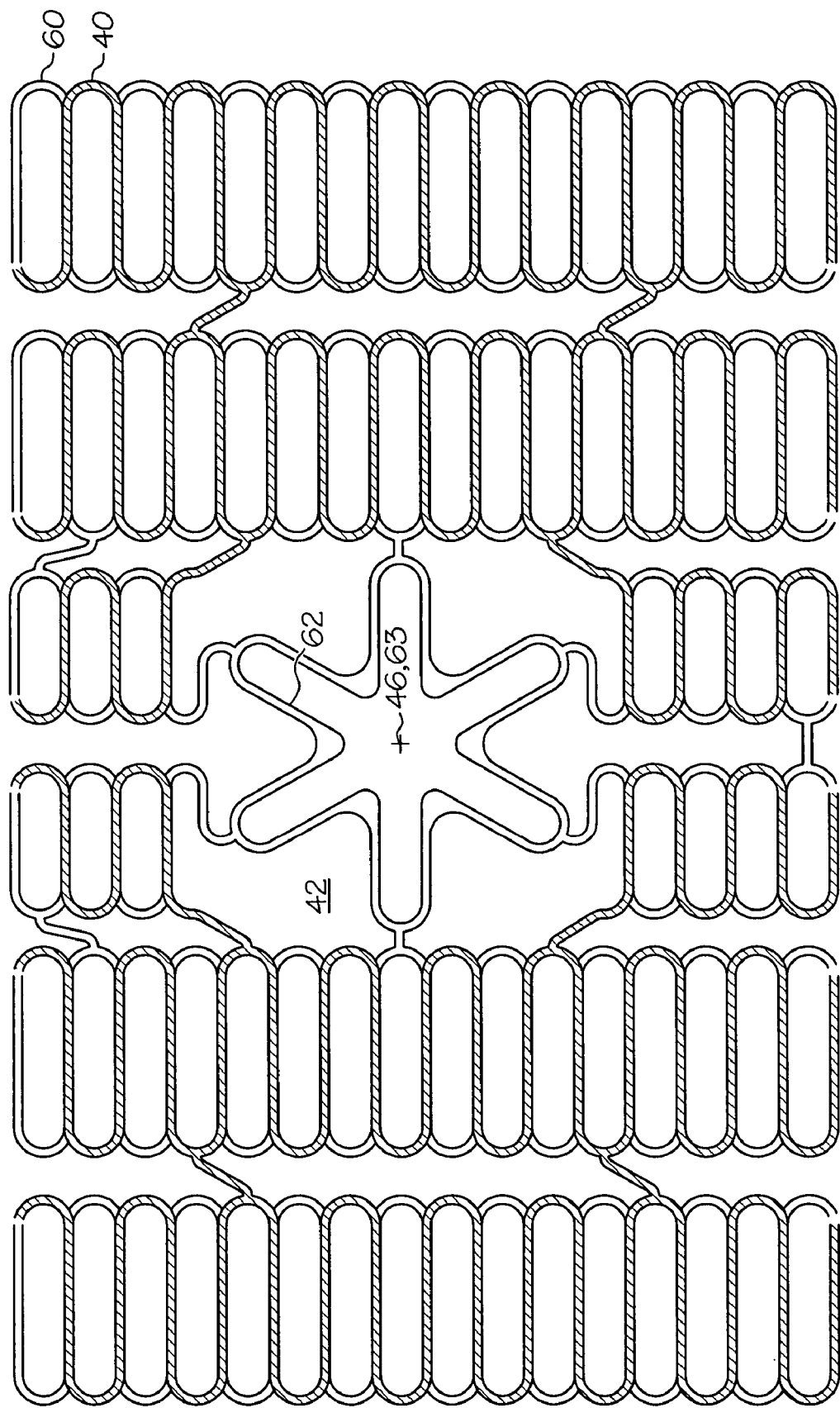

FIG. 2e shows a flat pattern for a medical device 10 similar to FIG. 2c, with the locations of the stent patterns 40, 60 reversed, such that the flat pattern for the first stent 40 may be positioned over the flat pattern for the second stent 60. While a person of ordinary skill in the art will recognize that the flat patterns of FIGS. 2c and 2e may each be selectively rolled to form a device wherein either stent 40, 60 may comprise the outer stent, FIG. 2e is shown for clarification purposes.

Figure 3B:
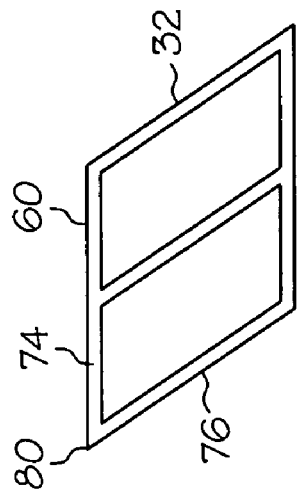
FIG. 3b shows another embodiment of stent structure suitable for use in a medical device.
Figure 3D:
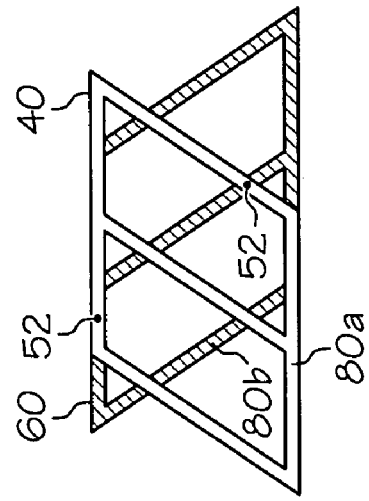
FIG. 3d shows a portion of another embodiment of a medical device comprising the stent structures of FIGS. 3a and 3b.
Figure 3A:
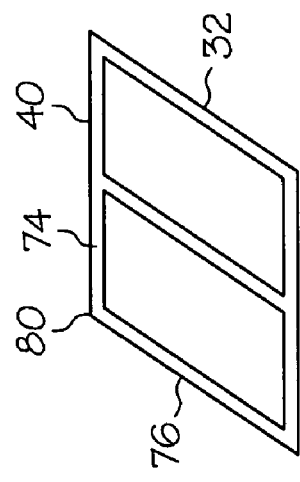
FIG. 3a shows another embodiment of stent structure suitable for use in a medical device.

FIG. 3a shows another embodiment of a portion of a stent pattern comprising a plurality of interconnected struts 32 which may be suitable for use as a first stent 40. The pattern may further comprise longitudinal struts 74 and joining struts 76, which may meet at an intersection 80.

FIG. 3b shows another embodiment of a portion of a stent pattern comprising a plurality of interconnected struts 32 which may be suitable for use as a second stent 60. The pattern of the second stent 60 may comprise a mirror image of the pattern of the first stent 40 as depicted in FIG. 3a. Thus, the joining struts 76 shown in FIG. 3b may be canted with an orientation that is reversed from the orientation shown in FIG. 3a.

Figure 3C:
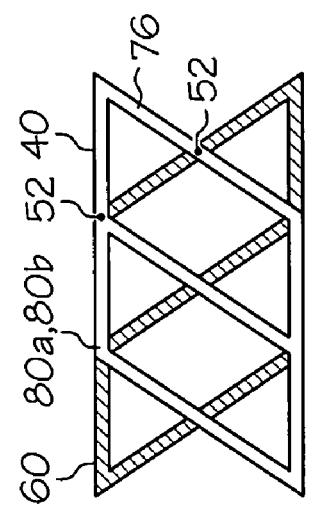
FIG. 3c shows a portion of an embodiment of a medical device comprising the stent structures of FIGS. 3a and 3b.

FIG. 3c shows a portion of an embodiment of a medical device 10 comprising the stent patterns 40, 60 of FIGS. 3a and 3b. The first stent 40 may overlap the second stent 60. The stents 40, 60 may be oriented such that an intersection 80a between a longitudinal strut 74 and a joining strut 76 of the first stent 40 is aligned with an intersection 80b of the second stent 60.

Connections 52 between the stents 40, 60 may be placed in any suitable locations, such as where intersections 80a, 80b meet, and/or at locations where joining struts 76 cross.

FIG. 3d shows a portion of another embodiment of a medical device 10 comprising the stent patterns 40, 60 of FIGS. 3a and 3b. The first stent 40 may overlap the second stent 60. The location of the first stent 40 with respect to the second stent 60 may be offset from the location shown in FIG. 3c. In the embodiment of FIG. 3d, intersections 80a of the first stent 40 may be offset from intersections 80b of the second stent.

In some embodiments of a medical device comprising a first stent 40 and a second stent 60, the second stent 60 may comprise a partial stent or a plurality of struts connected to the first stent 40 in select locations to provide additional vessel support at select locations of the medical device 10.

Figure 4:
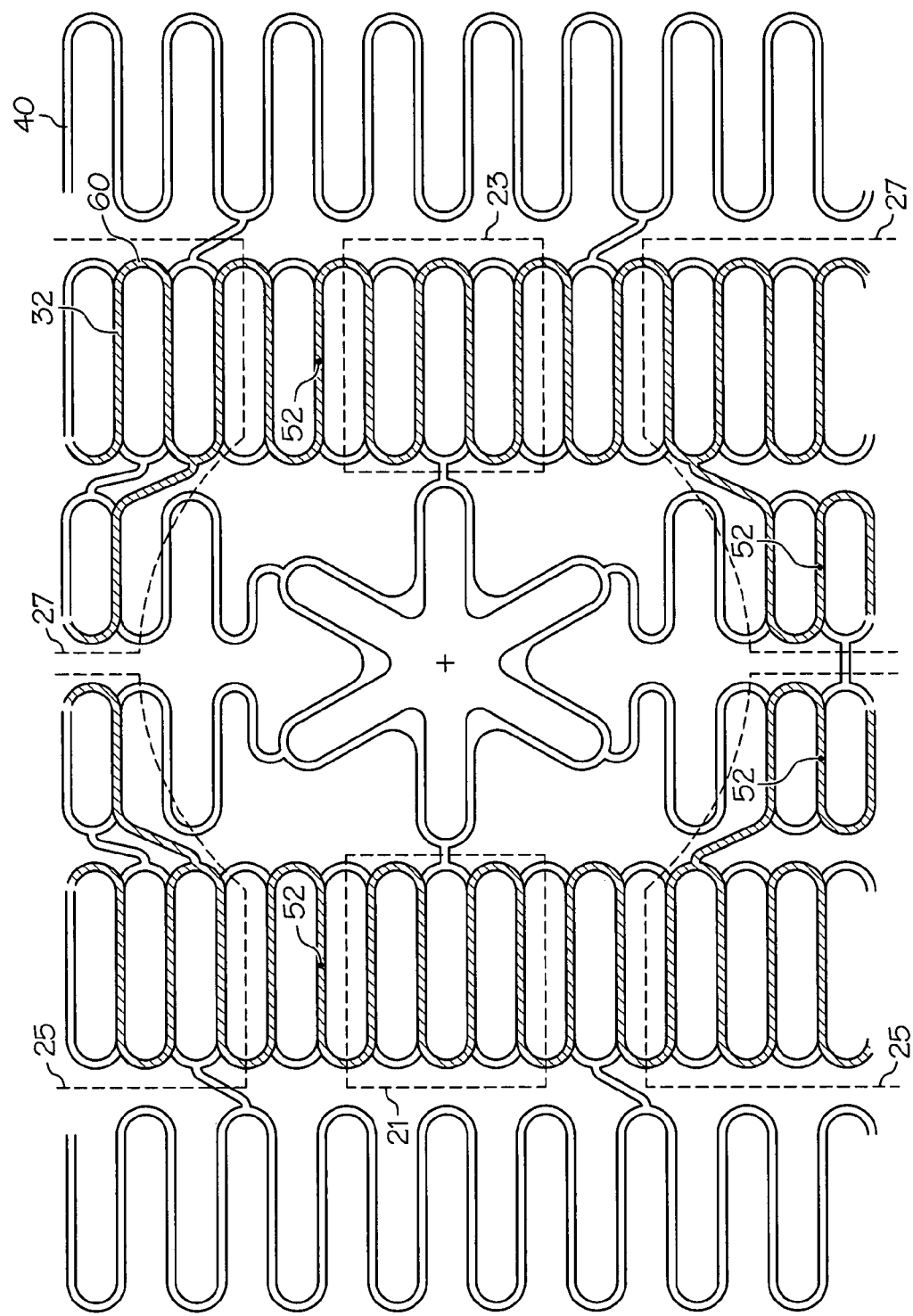
FIG. 4 shows a flat pattern for another embodiment of a medical device.

FIG. 4 shows an embodiment of a flat pattern for a medical device 10 comprising a first stent 40 and a second stent 60. The second stent 60 may comprise interconnected struts 32 that are selectively designed to provide additional vessel support at predetermined locations. The first stent 40 and the second stent 60 may be connected by at least one and desirably a plurality of connections 52 as herein described.

Struts 32 of the second stent 60 may have any suitable size and shape. Struts 32 of the second stent 60 may be located in proximity to any portion of the first stent 40 and may provide addition vessel support in any suitable location. The embodiment of FIG. 4 includes struts 32 oriented to provide additional vessel support to an area 21 adjacent to the ostium near the contralateral ostial wall, an area 23 adjacent to the ostium near the carina 23, an area 25 opposite the ostium and contralateral ostial wall, and an area 27 opposite the ostium and carina as also depicted in FIG. 1.

Figure 5:
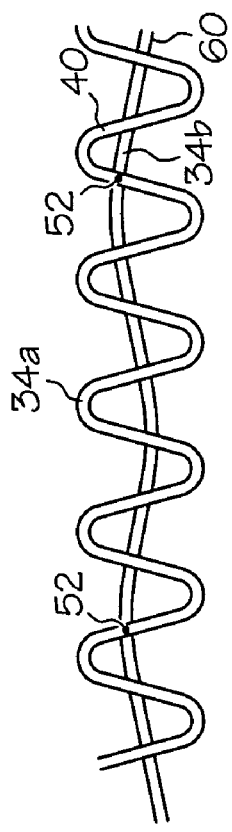
FIG. 5 shows a portion of a flat pattern for another embodiment of a medical device.

FIG. 5 shows an example of another embodiment of structure of a first stent 40 and a second stent 60 that may be used to form a medical device. The stents 40, 60 may be connected by at least one connection 52. The first stent 40 may include a serpentine band 34a having a predetermined wavelength, frequency and amplitude. The second stent 60 may include a serpentine band 34b that may have a wavelength, frequency and/or amplitude that is different from the serpentine band 34a of the first stent 40.

In some embodiments, the wavelength, frequency and/or amplitude of a serpentine band 34 of either stent 40, 60 may change.

In some embodiments, any area of a medical device 10 may include areas where one stent 40, 60 has a greater strength than the other stent. In some embodiments, a first stent 40 may be stronger than a second stent 60 in some areas, and the second stent 60 may be stronger than the first stent 40 in other areas. In various embodiments, a stronger stent may have any suitable design to provide the greater strength, such as being made from a different material, having larger strut members, such as wider or thicker struts, etc. In some embodiments, a first stent 40 may comprise a plurality of interconnected struts designed primarily to provide a high amount of vessel support, while a second stent 60 may comprise a plurality of interconnected struts designed primarily to provide structural strength.

Figure 6:
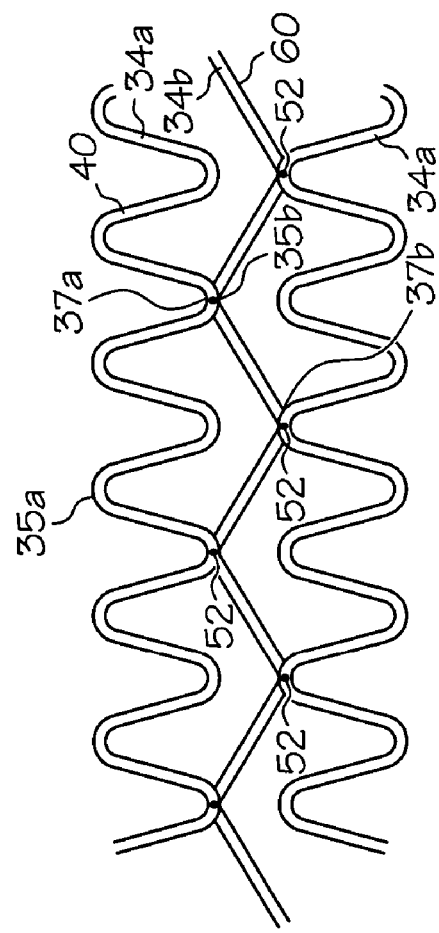
FIG. 6 shows a portion of a flat pattern for another embodiment of a medical device.

FIG. 6 shows a portion of another embodiment of a medical device 10 comprising a first stent 40 and a second stent 60. Each stent 40, 60 may include serpentine bands 34 comprising alternating proximal turns 35 and distal turns 37. Connections 52 between the stents 40, 60 may be located where a turn 35a, 37a of the first stent 40 meets a turn 35b, 37b of the second stent 60. For example, a connection 52 may be located where a distal turn 37a of the first stent 40 meets a proximal turn 35b of the second stent 60.

A second stent 60 may include a serpentine band 34b that connects in one or more locations to one serpentine band 34a of the first stent 40 and in one or more locations to another serpentine band 34a of the first stent 40.

A medical device 10 may include stents 40, 60 having any suitable strut design. Some stent designs which include stent side branch structure 62 (see FIG. 1) are described in U.S. patent application Ser. Nos. 11/138,022, 11/138,202 and 11/138,196, the entire disclosures of which are hereby incorporated herein in their entireties.

In some embodiments, both stents 40, 60 may include side branch structure 62, and the side branch structure of one stent desirably compliments the design of the side branch structure of the other stent to provide vessel support to areas such as the carina and contralateral ostial wall.

A first stent 40 and a second stent 60 may further include complimentary designs over at least a portion of the medical device 10. Some further examples of complimentary stent designs suitable for use as inner and outer connected stents are described in U.S. patent application Ser. No. 10/864,665, the entire disclosure of which is hereby incorporated herein in its entirety.

Figure 7:
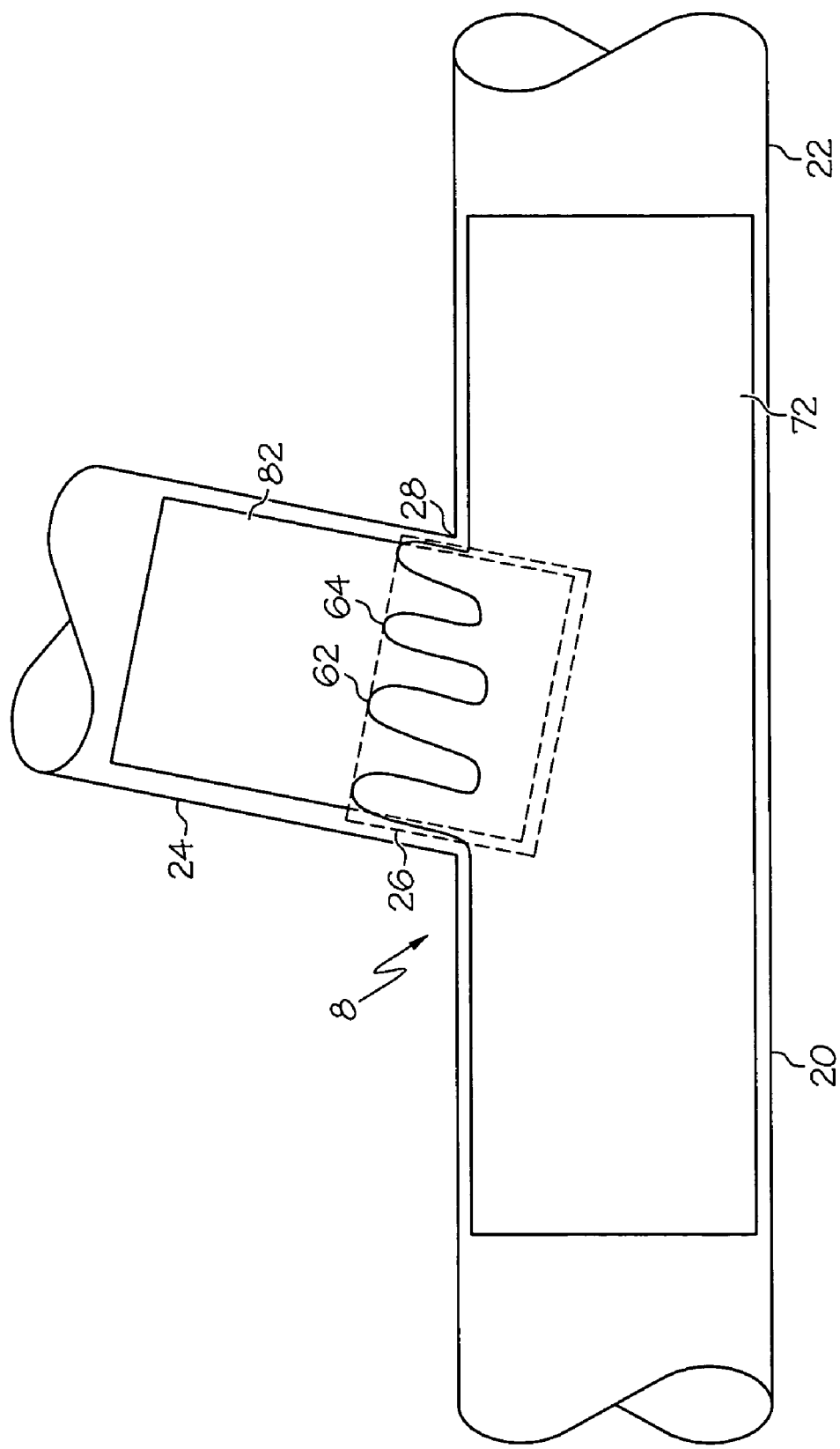
FIG. 7 shows an embodiment of a medical device oriented within a vessel.

FIG. 7 shows an embodiment of a medical device 8 oriented within a bodily vessel 20. The medical device 8 may comprise a main branch portion 72 and a side branch portion 82. Each portion 72, 82 may comprise a stent, a graft, a stent-graft or any other suitable vessel supporting structure.

The main branch portion 72 may include a side branch structure 62 having outwardly deployable petals 64 and may comprise an embodiment of a medical device 10 as herein described, which may include a first stent 40 and a second stent 60 (see FIG. 2c). In some embodiments, the main branch portion 72 may comprise any suitable portion of a medical device 10 as described herein, such as a first stent 40 or a second stent 60, or any other suitable stent structure.

The side branch portion 82 may comprise any suitable stent structure, for example comprising a plurality of interconnected struts. In some embodiments, a stent oriented in a side branch vessel 24 may include structure that extends into the main branch vessel 22, for example as disclosed in U.S. Pat. No. 6,896,699, the entire disclosure of which is hereby incorporated herein in its entirety.

Areas where structure of the main branch portion 72 and side branch portion 82 overlap 16 desirably provide increased vessel coverage and support. Thus, the overlap may provide increased support in areas such as the contralateral ostial wall 26 and areas near the carina 28.

Desirably, a line oriented in a radial direction of the side branch portion 82 in some locations of the overlap 16 may pass through a cell of the side branch portion 82 and intersect a strut of the main branch portion 72. In some other locations, a radial line may pass through a cell of the main branch portion 72 and intersect a strut of the side branch portion 82. In other locations, a radial line may pass through cells of both portions 72, 82. In still other locations, a radial line may intersect struts of both portions 72, 82.

In some embodiments, at least a portion of interconnected struts of the side branch portion 82 may be shaped similarly to a portion of interconnected struts of the main branch portion 72. In some embodiments, at least a portion of interconnected struts of the side branch portion 82 may comprise a mirror image of a portion of interconnected struts of the main branch portion 72.

The main branch portion 72 may be delivered to a deployment location and deployed, which may comprise increasing the diameter of the main branch portion 72, and may further comprise deploying the side branch structure 62 outwardly into a side branch vessel 24. The side branch portion 82 may be delivered to its deployment location relative to the main branch portion 72, and may be deployed, which may comprise increasing the diameter of the side branch portion 82. In some embodiments, deployment of the side branch portion 82 may further comprise orienting the side branch portion 82 such that struts of the side branch portion 82 mesh with struts of the main branch portion 72 to provide additional vessel coverage. In some embodiments, deployment of the side branch portion 82 may further comprise properly orienting any portion of the side branch portion 82 which extends into the main branch vessel 22.

The invention is also directed to delivery systems used in delivering a medical device 10 to a deployment location, and to methods of stenting a bifurcation using a medical device 10 as described herein.

Figure 8:
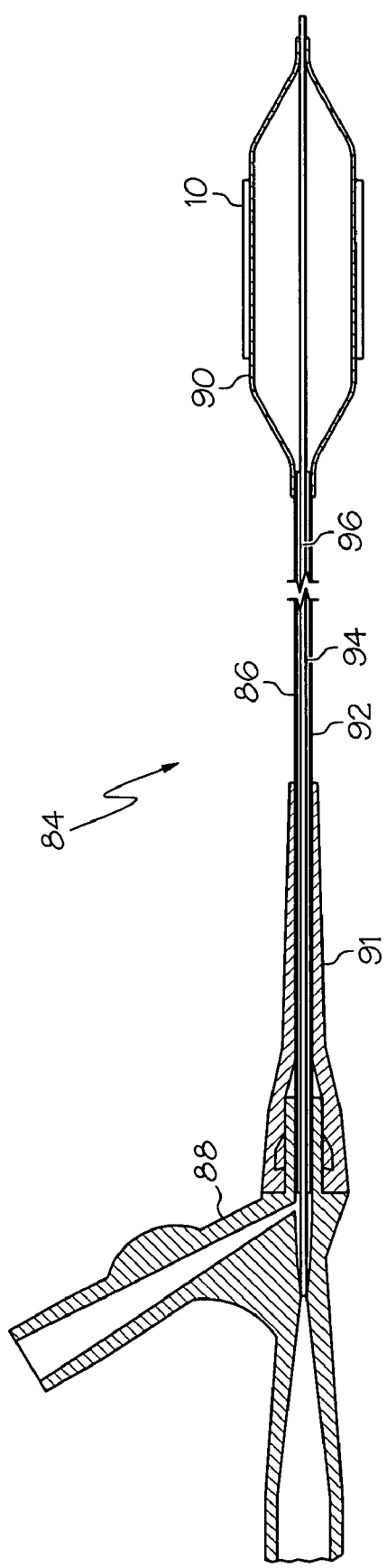
FIG. 8 shows an embodiment of a delivery system suitable for use with a medical device.

FIG. 8 shows a longitudinal cross-sectional view of an example of a catheter assembly 84 that is representative of an over-the-wire (OTW) or single-operator-exchange (SOE) angioplasty balloon catheter. Such balloon catheters are discussed, for example, in U.S. Pat. Nos. 6,113,579, 6,517,515 and 6,514,228, the entire disclosures of which are incorporated herein by reference in their entireties. The catheter 84 may include an elongate shaft assembly 86 and an OTW-type manifold assembly 88 connected to a proximal end of shaft assembly 86. The manifold assembly 88 may further comprise a strain relief device 91. The shaft assembly 86 may comprise an outer tube 92 coaxially disposed about an inner tube 94. The inner tube 94 may include an interior lumen which may comprise a guide wire lumen. An area between the inner tube 94 and the outer tube 92 may comprise an inflation lumen 96 which may be in fluid communication with an interior portion of an inflation balloon 90. FIG. 8 is provided only as an example of one type of catheter assembly suitable for use with a medical device 10, and is not intended to limit the scope of the present invention.

Figure 9:
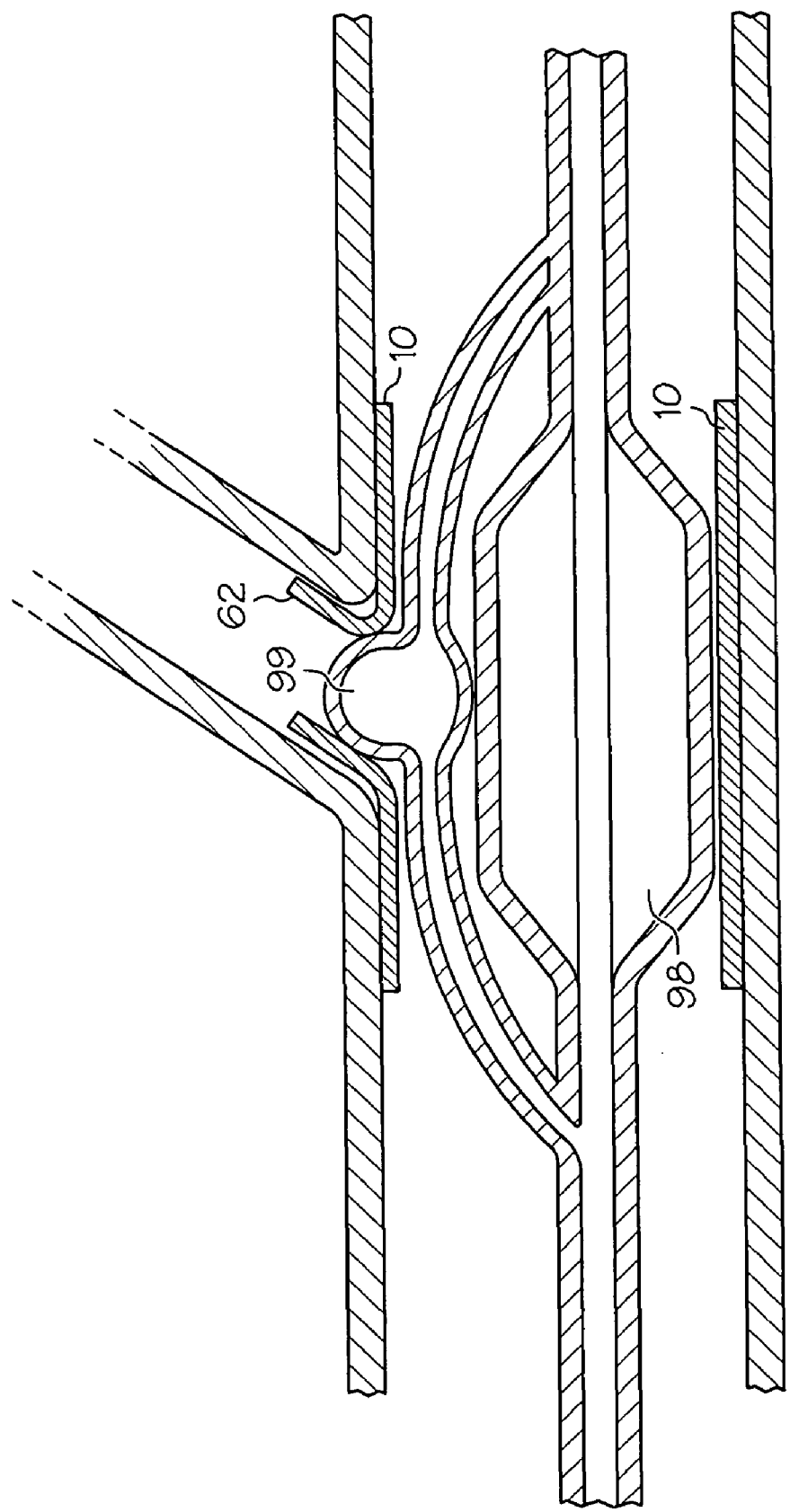
FIG. 9 shows another embodiment of a delivery system suitable for use with a medical device.

FIG. 9 shows another embodiment of a catheter assembly 84 that may be used in delivering a medical device 10 to a deployment site. The assembly 84 may include a first inflatable portion 98 and a second inflatable portion 99. The second inflatable portion 99 may be used to deploy the side branch structure 62 of a medical device 10 into a side branch vessel. Similar catheter assemblies and methods of use are disclosed in US Published Application No. 20050060027, the entire disclosure of which is hereby incorporated herein by reference in its entirety.

The inventive medical devices may be made from any suitable biocompatible materials including one or more polymers, one or more metals or combinations of polymer(s) and metal(s). Examples of suitable materials include biodegradable/bioabsorbable materials that are also biocompatible. The term biodegradable is intended to mean that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol. Further materials may include MRI compatible materials such as niobium-zinc.

The inventive medical devices may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive medical devices may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the medical device, the delivery system or other portion of the assembly may include one or more areas, bands, coatings, members, etc. that is (are) detectable by imaging modalities such as X-Ray, MRI, ultrasound, etc. In some embodiments, the entire stent may be MRI compatible. In some embodiments at least a portion of the stent and/or adjacent assembly is at least partially radiopaque.

In some embodiments the at least a portion of the medical device is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS) polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A medical device comprising:
   a first stent and a second stent, each stent comprising a tubular framework of interconnected struts, at least a portion of the second stent oriented within the first stent in both unexpanded and expanded states of the medical device, the first stent and the second stent coaxially aligned such that a central axis of the first stent and a central axis of the second stent are collinear;
   the medical device further comprising an outwardly deployable side branch structure comprising a plurality of petals.

2. The medical device of claim 1, wherein the first stent comprises the side branch structure and the second stent further comprises a side branch opening.

3. The medical device of claim 1, wherein the second stent comprises the side branch structure and the first stent further comprises a side branch opening.

4. The medical device of claim 3, wherein at least a portion of the side branch structure of the second stent extends through the side branch opening of the first stent when the stent is deployed.

5. The medical device of claim 1, wherein the first stent comprises a first strut pattern and the second stent comprises a second strut pattern that is different from the first strut pattern.

6. The medical device of claim 1, wherein at least a portion of the second stent comprises a mirror image of a portion of the first stent.

7. The medical device of claim 1, wherein the first stent is connected to the second stent by at least one connection, said connection selected from a group consisting of a weld or solder connection; an adhesive connection; a suture; a collar; a rivet; a pin; a cooperative tab and notch; and a hook and loop fastener.

8. An assembly comprising:
   a delivery catheter comprising a catheter shaft having an inner lumen; and
   the medical device of claim 1, wherein the medical device is oriented about a distal portion of the catheter shaft.

9. The assembly of claim 8, wherein the delivery catheter further comprises an inflation balloon, at least a portion of the medical device oriented about the inflation balloon.

10. A medical device comprising:
    a first stent comprising a plurality of interconnected struts, the struts defining a plurality of cells, the stent further comprising a side branch opening, the side branch opening comprising a cell having a different shape than other cells of the stent;
    a second stent comprising a plurality of interconnected struts, the second stent defining a first end region, a central region and a second end region, said first end region and said second end region each comprising at least one serpentine band, the struts defining a plurality of cells, the central region further comprising a side branch structure having at least one outwardly deployable petal;
    wherein at least the central region of the second stent is disposed concentrically within the first stent, and in an expanded state, only said at least one outwardly deployable petal extends outwardly above an outer surface of said first stent in a stent radial direction.

11. The medical device of claim 10, wherein the first stent and the second stent are coaxially aligned.

12. The medical device of claim 10, wherein the side branch opening of the first stent extends around the side branch structure of the second stent.

13. The medical device of claim 10, wherein a center of the side branch opening of the first stent is coaxially aligned in a stent radial direction with a center of the side branch structure of the second stent.

14. The medical device of claim 10, wherein the second stent and the first stent are concentric for an entire length of the medical device.

15. The medical device of claim 10, wherein at least a portion of the plurality of interconnected struts of the second stent comprises a mirror image of at least a portion of the plurality of interconnected struts of the first stent.

16. The medical device of claim 10, wherein the first stent is connected to the second stent by at least one connection, said connection selected from a group consisting of a weld or solder connection; an adhesive connection; a suture; a collar; a rivet; a pin; a cooperative tab and notch; and a hook and loop fastener.

17. The medical device of claim 16, wherein the first stent comprises a first band strut, the second stent comprises a second band strut, and the connection connects a midpoint of the first band strut to a midpoint of the second band strut.

18. The medical device of claim 16, wherein the first stent comprises longitudinal struts and joining struts, the joining struts extending between adjacent longitudinal struts, and the connection is located at an intersection of a longitudinal strut and a joining strut.

19. A method of stenting a vessel comprising:
    providing a delivery catheter having an expandable medical device oriented about a distal end, the medical device comprising:
        a first stent and a second stent, at least a portion of the second stent oriented within the first stent, the second stent coaxially aligned with the first stent such that a central axis of the first stent and a central axis of the second stent are collinear, the medical device further comprising an outwardly deployable side branch structure comprising a plurality of petals;
    delivering the medical device to a deployment location in a bodily vessel; and
    expanding the medical device by expanding the first stent and the second stent simultaneously.

20. The method of claim 19, further comprising expanding the outwardly deployable
    side branch structure into a side branch vessel.

* * * * *